(12) United States Patent
Zhu et al.

(10) Patent No.: US 9,181,166 B1
(45) Date of Patent: Nov. 10, 2015

(54) CATALYTIC METHOD FOR QUANTITATIVE HYDROLYTIC DEPOLYMERIZATION OF LIGNOCELLULOSES IN ONE-POT

(71) Applicants: Zuolin Zhu, San Diego, CA (US); Jonathan Zhu Zhu, San Diego, CA (US)

(72) Inventors: Zuolin Zhu, San Diego, CA (US); Jonathan Zhu Zhu, San Diego, CA (US)

(*) Notice: Subject to any disclaimer, the term of this patent is extended or adjusted under 35 U.S.C. 154(b) by 0 days.

(21) Appl. No.: 14/492,278

(22) Filed: Sep. 22, 2014

(51) Int. Cl.
*C07C 51/06* (2006.01)
*C07C 51/00* (2006.01)
*C07C 39/235* (2006.01)
*C07C 309/43* (2006.01)

(52) U.S. Cl.
CPC ............ *C07C 51/00* (2013.01); *C07C 39/235* (2013.01); *C07C 309/43* (2013.01); *C07C 2103/24* (2013.01)

(58) Field of Classification Search
None
See application file for complete search history.

(56) References Cited

U.S. PATENT DOCUMENTS

2011/0180752 A1* 7/2011 Zhu et al. .................. 252/182.31
2013/0123547 A1* 5/2013 Zhu ........................... C08H 8/00
568/652

FOREIGN PATENT DOCUMENTS

CN 102199086 * 9/2011

OTHER PUBLICATIONS

Machine Translation of CN 102199086 provided by Espacenet at http://worldwide.espacenet.com/.*
Zhu et al., Bioresource Technology 128 (2013) 229-234.*
Machine Translation of CN 102199086.*
Machine Translation of CN 102020556.*

* cited by examiner

*Primary Examiner* — Karl J Puttlitz (57) ABSTRACT

Lignocelluloses are selectively hydrolyzed into only two kinds of products in an one-pot, quantitative reaction. Lignin is reduced into small molecular aromatics without using reductants. Simultaneously, cellulose and hemicellulose are oxidized into small organic acids without using oxidants. A catalytic method is invented for oxygen-transfer from lignin to cellulose or hemicellulose. There is neither gasification nor black tar formation observed during the hydrolytic depolymerization.

7 Claims, 4 Drawing Sheets

CATALYTIC METHOD FOR QUANTITATIVE HYDROLYTIC DEPOLYMERIZATION OF LIGNOCELLULOSES IN ONE-POT

FIELD OF THE INVENTION

The present invention relates to a novel catalytic method for the hydrolytic depolymerization of lignocelluloses into liquid products quantitatively in a one-pot reaction, particularly the simultaneous conversion of lignin into small molecular aromatics, cellulose and/or hemicellulose into small organic acids.

DESCRIPTION OF RELATED ART

Global warming and the increasing cost of fossil oil stimulates the interest in the development of alternatives to petroleum-based chemicals, fuels, and other products. Lignocellulose is the most promising renewable alternative. Among all organic chemicals, small molecular aromatics are important components in liquid transportation fuels, and starting materials for high performance polymers. Currently, almost all small molecular aromatics are produced from petroleum oil using complicated technologies. With the increased yields of shale gas and methane hydrate that contain no aromatic components, the cost of producing aromatics is expected to increase.

Effectively breaking down polymers of lignocelluloses into small organic molecules, especially through the use of hydrolytic depolymerization, is considered to be the most cost effective method in making fuels, chemicals, and other products compared with those of petro-chemical processes. Many well-known methods for the depolymerization of lignocelluloses have been proved to be commercially impractical due to a high operation cost. Thermal-chemical methods, such as liquefaction, pyrolysis, etc., show no product selectivity. The product is a mixture of phenols, aldehydes, alcohols, acids, alkanes, olefins, esters, ethers, etc. These methods always result in the formation of black tar and low yields of liquid products. Bio-chemical methods require component separation/isolation and purification, which show a huge loss of organic carbon in percentage and a slow rate of cellulose depolymerization. All known methods that involve lignin isolation followed by depolymerization and deoxygenation have been proved to be commercially ineffective (Chem. Rev., 2010, volume 110, 3552-3599). Hydrogenation is the only known method for lignin depolymerization that produces a reasonable amount of liquid product, but the reaction conditions are harsh, and a superfluous amount of organic solvents were used for decomposition. A novel method is needed for an efficient hydrolytic depolymerization of lignocelluloses, with good product selectivity, no need for component separation/isolation and purification, and without hydrogen and organic solvents used during depolymerization process.

Small molecular aromatics are one of the most important organic chemicals. They are the key components in transportation liquid fuels; they are used as octane number enhancers; they are the ingredients to reduce emission of nitrogen oxides; they are used to meet the minimum energy density requirement, and to prevent fuel leaks by making the elastomers swell in fuel systems. They are also the starting materials for the production of high performance polymers. These polymers possess desired qualities such as corrosive resistance, extreme weather endurance, and wear and tear resistance, etc. Currently, almost all aromatics are made from fossil oils or coals. Lignins are the only renewable resource of aromatics, and due to the lack of an economical method for depolymerization, it is considered that lignin can be used to make anything but money at the moment.

Most organic acids are currently produced using petrochemical processes or fermentation methods from sugar. Organic acids are important commodity products with broad applications in many areas. For example, esters are better solvents for paints and ink than alkane-based organic solvents, because esters are biodegradable and have excellent dissolving power (US Pat., 2010/0184896 A1, 2010). Esters are also effective liquid fuels, possessing a higher or similar heat of combustion, and better anhydrous product yields, than that of ethanol. Additionally, they are non-toxic and, unlike ethanol, non-corrosive. Organic acids can also be converted into many useful chemicals. For example, lactic acid can be converted into n-propanol, 1,2-propanediol, acrylic acid, propanoic acid, etc. Until now there is no cost effective method for making small organic acids from biomass. Alkaline hydrothermal methods produce a mixture of products containing more than a hundred different chemicals. Another problem regarding the disproportionation reaction is that it has no specificity in terms of products; the product mixture contains more than 25 monocarboxylic acids, 22 dicarboxylic acids, and several cyclopentyl chemicals. With oxidation methods (Jin, F. M., and Enomoto, H., 2009, BioResources volume 4, 704-713) strong oxidants have to be used at elevated temperatures, such as concentrated hydrogen peroxide (Zhou, Z., et al, 2006, J. Mater. Sci. Volume 41, 1501-1507; Jin, F. M., et al, 2001, J. Supercrit. Fluid. Volume 19, 251-262) and nitric acid (Fisher, K., and Bipp, H. P., 2005, Bioresour. Technol. Volume 96, 831-842). There are safety issues using strong oxidants with these processes. Additionally, multi-hydroxyl organic acids, such as tartaric acid, glucaric acid, gluconic acid, and threonic acid, are formed. Multi-hydroxyl organic acids are difficult to isolate and purify, therefore, their use is limited.

A cost effective method is needed for efficiently converting all organic polymers of lignocelluloses, such as cellulose, lignin, and hemicellulose, into small organic molecules without lignocellulosic component separation/isolation and purification. Small organic molecules are better suited for producing fuels, chemicals, and other products.

SUMMARY OF THE INVENTION

It is the primary object of the present invention to provide a novel catalytic method for one-pot, selective, hydrolytic depolymerization of lignocelluloses into liquid products quantitatively without lignocellulosic component separation/isolation and purification. In this disclosed invention, through one-pot reaction, lignin is selectively converted into small molecular aromatics in quantitative yields. In the same time, cellulose and hemicellulose are transformed selectively into products that consist exclusively of simple organic acids, such as formic acid, acetic acid, glycolic acid, lactic acid, and succinic acid—with lactic acid content up to 50%. Neither strong reductants such as hydrogen nor strong oxidants such as hydrogen peroxide are needed for the selective one-pot hydrolytic depolymerization. Neither gasification nor black tar formation is observed during the catalytic one-pot hydrolytic depolymerization.

One aspect of the invention is the requirement for the composition of lignocelluloses. According to the invention, "R" is defined as the ratio between lignin, cellulose and hemicellulose.

$$R = \frac{\text{mass weight of lignin}}{\text{mass weight of cellulose} + \text{mass weight of hemicellulose}}$$

when R=0.5 or higher, 100% of lignocelluloses are depolymerized into small organic molecules.

According to the invention, unlike all other known methods, there are almost no phenols observed, such as phenol, methoxy phenols, alkyl phenols, etc. Phenols are known for their high refractory against deoxygenation and thermal formation of gums and char upon heating at a typical hydrotreatment temperature.

According to the invention, the method generally involves: (1) mixing particles of lignocelluloses with catalyst in water; (2) carrying the reaction of mixtures at a desired temperature and proper pressure.

The reaction temperature of hydrolytic depolymerization may be greater than 190° C., but less than 280° C. The pressure of the reaction will be higher than the saturated vapor pressure of the solvent at the reaction temperature, in order to maintain the reaction system in liquid state.

The catalyst for the one-pot hydrolytic depolymerization consists of the metallic salts of 9,10-dihydroxyanthracene and its derivatives. These derivatives include but not limited to: 1,2-, 1,4-, 9,10-, 2,6-dihydroxyanthracene, 2-ethyl-9,10-dihydroxyanthracene, 1-nitro dihydroxyanthracene, dihydroxyanthracene-1-sulfonic acid, dantron, emodin, aloe emodin, rufigallol, mitoxantrone, pixantrone, anthracyclines, dinitro-dihydroxyanthracene, C. I. Acid Blue 43, C. I. Vat Violet 1, C. I. Disperse Red 60, etc. All metallic salts can be used; however, potassium, sodium, and calcium salts are preferred. The metallic salts of small molecular aromatics obtained from the hydrolytic depolymerization of lignocelluloses are effective catalysts.

sodium salt of 9,10-dihydoxyanthracene

DETAILED DESCRIPTION OF THE INVENTION

The present invention provides a novel catalytic method for selective hydrolytic depolymerization of lignocellulose into liquid products in one-pot reaction with quantitative conversion. All organic components of lignocellulose are simultaneously hydrolyzed into small organic molecules, without component separation/isolation and purification. For example, lignin is selectively converted into small molecular aromatics in quantitative yields, with the majority of these aromatics having molecular weights of less than 400 Da; cellulose, hemicellulose, pectin and starch are transformed selectively into products consisting exclusively of simple organic acids, such as formic acid, acetic acid, glycolic acid, lactic acid, and succinic acid, with lactic acid content up to 50%.

The present invention provides a novel method with the potential to conceive an economically effective technology for biorefining. This novel method has all the merits of the second generation technologies of biorefining (thermochemical methods, and bio-chemical methods), but overcomes the disadvantages of them. The disclosed method is easy to operate, and eliminates the loss of organic components of starting lignocelluloses. The reaction is fast with good product selectivity, and neither gasification nor black tar formation is observed during the one-pot hydrolytic depolymerization reaction. On the contrary, thermal-chemical methods have no product selectivity. The formation of black tar and gasification is always observed in large amounts, thus the process gives very low yields of liquid products. Bio-chemical methods have very low yields of products and the process involves many steps, such as pretreatment, cellulose purification, cellulose hydrolysis, and fermentation, etc.

As used herein, the term "lignocelluloses" refers to biomass products produced by plants, such as leaves, stalks, roots, seeds, etc. Lignocelluloses refers to materials that are composed of the major components of lignin, and/or cellulose, and/or hemicellulose.

In the present invention, good product selectivity is defined by the ascertainment of only two kinds of products from the hydrolytic depolymerization of lignocelluloses—small molecular aromatics and small organic acids. Unlike all other known methods, there are almost no observable phenols produced using this novel method, such as phenol, methoxy phenols, alkyl phenols, etc. This result is important because phenols are known for their high refractory against deoxygenation, and thermal formation of gums and char upon heating at typical hydrotreatment temperatures.

In the present invention, "good product selectivity" is defined when the small organic acid products consist exclusively of simple organic acids, such as formic acid, acetic acid, glycolic acid, lactic acid, fumaric acid, and succinic acid, with lactic acid content up to 50%.

According to the invention, the hydrolytic depolymerization is carried out in a one-pot reaction without lignocellulosic component separation/isolation and purification. The method generally involves: (1) mixing particles of lignocelluloses with catalyst in water; (2) reacting the mixtures at a desired temperature and proper pressure. Lignocelluloses can be chopped, shredded, pressed, grounded or processed to a particle size between 1-100 mm.

According to the invention, "R" is defined as the ratio between lignin, cellulose and hemicellulose.

$$R = \frac{\text{mass weight of lignin}}{\text{mass weight of cellulose} + \text{mass weight of hemicellulose}}$$

According to the invention, when R is 0.5 or higher, lignocelluloses are 100% hydrolyzed into small organic molecules.

In the present invention, the gradient reaction temperature of hydrolytic depolymerization is programmed as: from ambient temperature to 180±5° C. first, and remained at this temperature for about ten minutes, then from 180±5° C. to the temperature of hydrolytic depolymerization.

In the present invention, the reaction temperature of hydrolytic depolymerization may be greater than 190° C., but less than 280° C. The pressure of the reaction will be higher than the saturated vapor pressure of the water at the reaction temperature, in order to maintain the liquid state reaction system. For example, the pressure is 4 MPa or higher when the reaction temperature is 250° C.

In the present invention, the metallic salts of small molecular aromatics obtained from the hydrolytic depolymerization of lignocelluloses, is used as the catalysts for one-pot hydrolytic depolymerization of lignocelluloses into small organic chemicals in quantitative yield. The catalyst for the one-pot hydrolytic depolymerization also includes the metallic salts of 9,10-dihydroxyanthracene and its derivatives. These derivatives include, but are not limited to: 1,2-, 1,4-, 9,10-, 2,6-dihydroxyanthracene, 2-ethyl-9,10-dihydroxyanthracene, 1-nitrodihydroxyanthracene, dihydroxyanthracene-1-sulfonic acid, dantron, emodin, aloe emodin, rufigallol, mitoxantrone, pixantrone, anthracyclines, dinitrodihydroxyanthracene, C.I. Acid Blue 43, C.I. Vat Violet 1, C.I. Disperse Red 60, etc. All metallic salts can be used; however, potassium, sodium, and calcium salts are preferred.

Disulfonate Sodium Salt of
9,10-Dihydoxyanthracene

Example of the Derivatives

The following examples are included to demonstrate the preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Analysis of organic acids: The organic acids are analyzed using the following methods and conditions: HPLC, Agilent 1200, column: SB-AQ, 5 μm, 4.60×250 mm; mobile phase: 0.025M, pH=2.5 phosphate buffer solution, flow rate: 0.6 ml/min for 0-10 min, 0.6 ml/min to 1.2 ml/min from 10-15 min, 1.2 ml/min to 0.6 ml/min from 15-30 min, then at 0.6 ml/min for 45 minutes. A DAD detector is used at a wavelength 210 nm and a column temperature is kept at 30° C. The sample size is 5 μl and all organic acids had a retention time of less than 14 minutes.

All volatile products such as phenols are analyzed using GCMS: Agilent 7890 GC with Agilent 5975C MS; Column: DB-5, 30 m×0.25 mm×0.25 μm; Injector: 10:1 split, 250° C.; Carrier gas: helium at 1.0 ml/min; Temperature: 60° C. initial, hold 5 min, ramp at 2° C./min to 200° C., hold 5 min, ramp at 2° C./min to 280° C., hold 5 min; Detector: Agilent 5975C; transfer line temperature 280° C.; ion source temperature 230° C.; quadruple temperature 150° C.; mass range 40-500 ug; ionization voltage 70 ev; Injection volume 0.2 μl.

Molecular mass of small molecular aromatics: Source Type: APCI
APCI Vaporizer Temp (° C.): 500.00 Sheath Gas Flow (arb): 50.00
Aux Gas Flow (arb): 10.00 Sweep Gas Flow (arb): 5.00
Capillary Temp (° C.): 350.00 I Spray voltage (kv): 3.5
Capillary voltage (v): −31 Tube lens (V): −90

Example 1

To a 1 liter stainless steel autoclave equipped with mechanical stirrer, add 900 ml of distilled water, 18 g of chopped dry grape tree branches (2-10 mm size, contain 38% cellulose, 20% hemicellulose, 29% lignin, and 13% others), and 5 g of disulfonate sodium salt of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C., and stirred at this temperature for 50 min. After cooling to a temperature below 60° C., a brown colored solution is obtained (the color darkens after the mixture is exposed to air). Gas is sampled for GC analysis. There is no alkanes or alkenes are detected in gas phase, and only trace of carbon monoxide. So there is no gasification. Filtration shows no signs of solid material in the product solution, concluding that the percentage of hydrolytic depolymerization is about 100%.

GCMS analysis shows there are almost no phenols, such as phenol, o-methoxyphenol, 2,6-dimethoxyphenol, etc. HPLC analysis of the solution shows that only several small organic acids are formed, such as formic acid, glycolic acid, acetic acid, lactic acid, succinic acid, etc. It contains 5.2 grams of lactic acid, 1.7 grams of glycolic acid, 1.84 grams of formic acid, 0.2 grams of acetic acid, 0.4 grams of succinic acid, and the rest are 2-hydroxyl isobutyric acid, fumaric acid, etc.

Example 2

To a 1 liter stainless steel autoclave equipped with mechanical stirrer, add 900 ml of distilled water, 18 g of wheat straw powder (2-10 mm size, contain 40% cellulose, 26% hemicellulose, 22% lignin, and 12% others), and 5 g of disulfonate sodium salt of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C., and stirred at this temperature for 50 min. After cooling to a temperature below 60° C., a brown colored solution is obtained (the color darkens after the mixture is exposed to air). Gas is sampled for GC analysis. There is no alkanes or alkenes are detected in gas phase, and only trace of carbon monoxide. So there is no gasification. Filtration gives 4.3 g solid. The solid has water content 58%, so the hydrolytic depolymerization is 90% for wheat straw (1.8 g un-hydrolyzed solid).

GCMS analysis shows there are almost no phenols, such as phenol, o-methoxyphenol, 2,6-dimethoxyphenol, etc. HPLC analysis of the solution shows that only several small organic acids are formed, such as formic acid, glycolic acid, acetic acid, lactic acid, succinic acid, etc. It contains 6.0 grams of lactic acid, 2.1 grams of glycolic acid, 2.2 grams of formic acid, 0.3 grams of acetic acid, 0.5 grams of succinic acid, and the rest are 2-hydroxyl isobutyric acid, fumaric acid, etc.

Example 3

To a 1 liter stainless steel autoclave equipped with mechanical stirrer, add 900 ml of distilled water, 18 g of chopped dry grape tree branches (2-10 mm size, contain 38% cellulose, 20% hemicellulose, 29% lignin, and 13% others), and 5 g of disulfonate sodium salt of 9,10-dihydroxyanthracene. The autoclave is sealed, purged with nitrogen three times, then filled with nitrogen at a pressure of 0.2-1 MPa, heated to 180° C. and maintain at this temperature for ten minutes. The temperature is then increased to 250° C., and stirred at this temperature for 50 min. After cooling to a temperature below 60° C., a brown colored solution is obtained (the color darkens after the mixture is exposed to air). Gas is sampled for GC analysis. There is no alkanes or alkenes are detected in gas phase, and only trace of carbon monoxide. So there is no gasification. Filtration shows no signs of solid material in the product solution, concluding that the percentage of hydrolytic depolymerization is about 100%.

GCMS analysis shows there are almost no phenols, such as phenol, o-methoxyphenol, 2,6-dimethoxyphenol, etc. HPLC analysis of the solution shows that only several small organic acids are formed, such as formic acid, glycolic acid, acetic acid, lactic acid, succinic acid, etc. It contains 5.5 grams of lactic acid, 1.8 grams of glycolic acid, 1.66 grams of formic acid, 0.3 grams of acetic acid, 0.3 grams of succinic acid, and the rest are 2-hydroxyl isobutyric acid, fumaric acid, etc.

Figure 1:
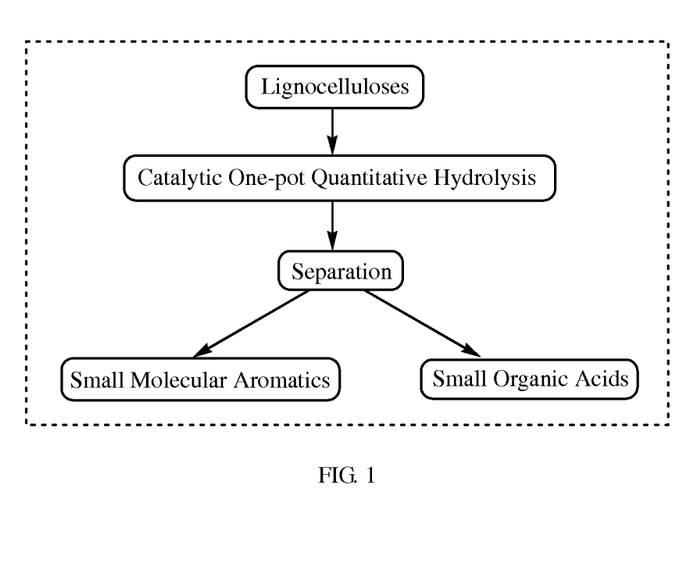
FIG. 1 illustrates the process scheme of the invented method.
Figure 2:
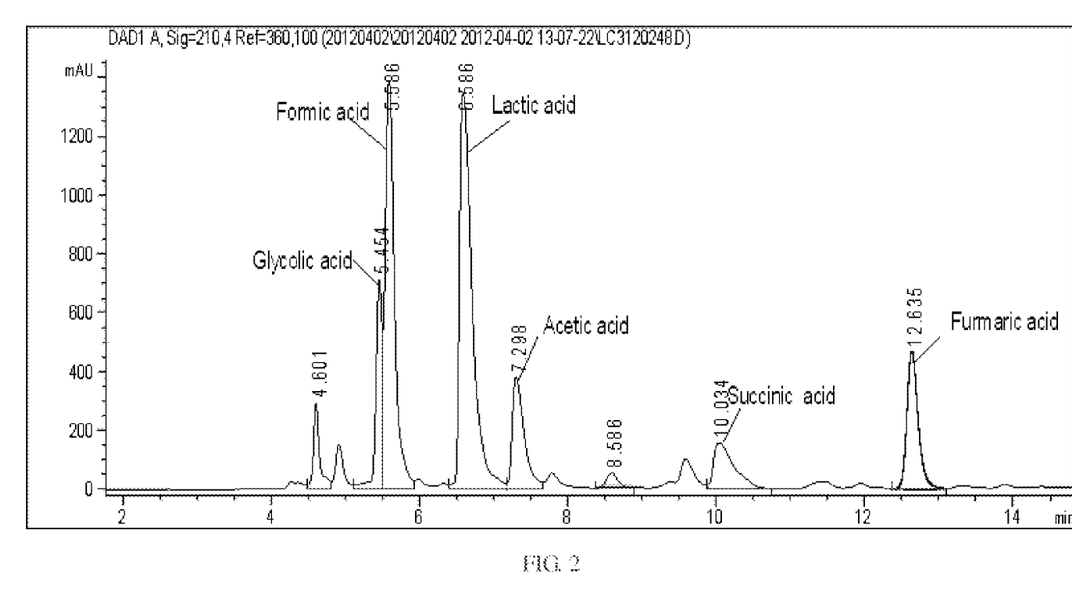
FIG. 2 illustrates the product distribution of small organic acids for the catalytic one-pot hydrolytic depolymerization of lignocellulose according to the present invention.
Figure 3:
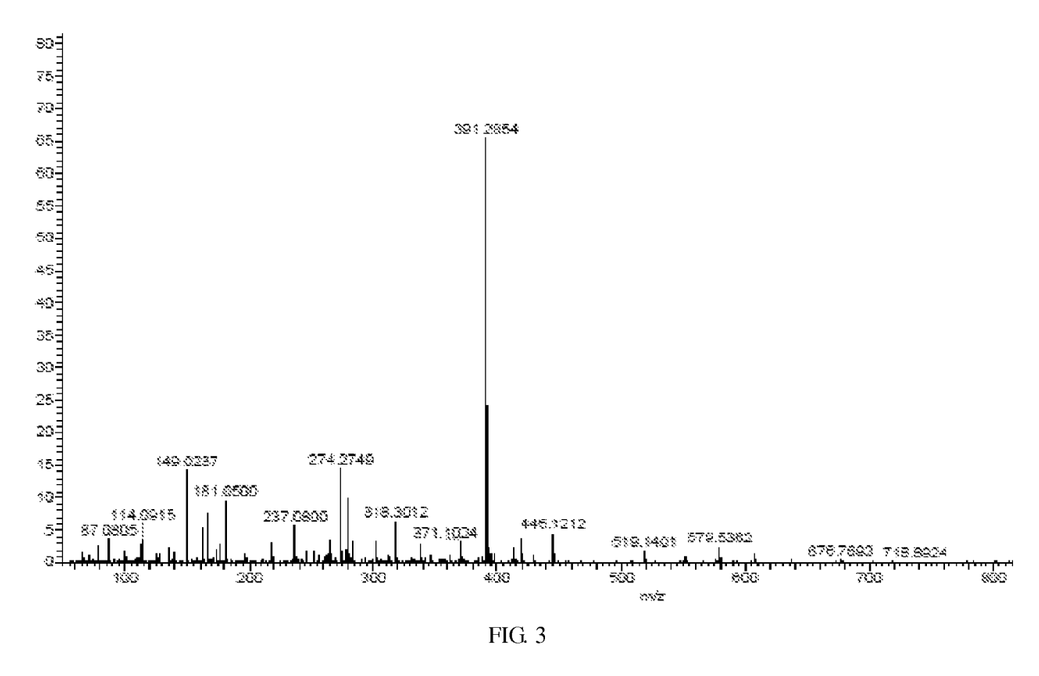
FIG. 3 is a typical molecular mass of small molecular aromatics from the catalytic one-pot hydrolytic depolymerization of lignocellulose according to the present invention.

The reaction solution is concentrated to about 100 ml under reduced pressure; the liquid obtained is mixed with equal volume of benzyl alcohol and acidified with formic acid to pH=4.2. The organic phase is separated and washed once with a half volume of water. HPLC analysis shows there is neither disulfonate sodium salt of 9,10-dihydroxyanthracene nor organic acid in organic solution. The benzyl alcohol is carefully removed under reduced pressure to obtain 20 g of sticky products (Product A). GC analysis shows it contains 73.3% benzyl alcohol. The weight of the small aromatics obtained is 5.4 g—its yield is 100% based on lignin weight. Molecular mass analysis shows they are mixtures (FIG. 3), most of which with a molecular weight between 162 to 340. GC analysis shows there are no phenol, methoxyphenol, and 2,6-dimethoxyphenol. Elemental analysis shows the oxygen content of this product is 18%, far below the oxygen content of lignin (~36%). This result suggests that our invented method is a catalytic oxygen-transfer reaction; oxygen atoms are transferred from lignin (products from lignin have reduced oxygen content) to cellulose or hemicellulose (products from cellulose and hemicellulose have increased oxygen content).

After extraction with benzyl alcohol, the aqueous phase is combined with water solution from washing benzyl alcohol extract, acidified with formic acid to pH=2.0 first, then water is carefully removed with toluene to obtain 16.2 g of organic acid products. There is almost no water left, and toluene content is less than 1%. Subtract the weight of catalyst, the yield of organic acid is about 100%.

Example 4

The experiments are carried out using the procedure described in example 1. Two parallel experiments are carried out. In one reaction, the reaction temperature is raised to 250° C. directly and stirred at this temperature for 50 min; in another reaction, the reaction mixture is heated to 180° C., maintained at this temperature for ten minutes, then increased to 250° C. and stirred for 50 min. Biomass used in this example is 18 g of chopped dry grape tree branches (2-10 mm size, contain 38% cellulose, 20% hemicellulose, 29% lignin, and 13% others), and the catalyst is 5 g of disulfonate sodium salt of 9,10-dihydroxyanthracene. After cooling to a temperature below 60° C., a brown color solution is obtained (the color turns deeper after the mixture is exposed to air). Gas is sampled for GC analysis. There is no alkanes or alkenes are detected in gas phase, and only trace of carbon monoxide. So there is no gasification. Filtration shows there is no solid material left in the product solution for both experiments. It means the hydrolysis percentage is about 100% for both experiments.

The analysis shows there is almost no difference between both experiments for major products of small organic acids. The major difference is the yield of lactic acid and the molecular weight of small molecular aromatics.

For the hydrolytic depolymerization reaction that is maintained at the temperature of 180° C. for ten minutes, the major organic acids are lactic acid (5.6 grams), glycolic acid (1.7 grams), formic acid (1.66 grams), acetic acid (0.3 grams), succinic acid of (0.2 grams), and the rest are 2-hydroxyl isobutyric acid, fumaric acid, etc. For the hydrolytic depolymerization reaction that the reaction temperature is raised to 250° C. directly, the major organic acids are lactic acid (3.6 grams, the yield of lactic acid is much lower), glycolic acid (1.9 grams), formic acid (1.7 grams), acetic acid (0.5 grams), succinic acid of (0.6 grams), and the rest are 2-hydroxyl isobutyric acid, fumaric acid, etc.

Figure 4:
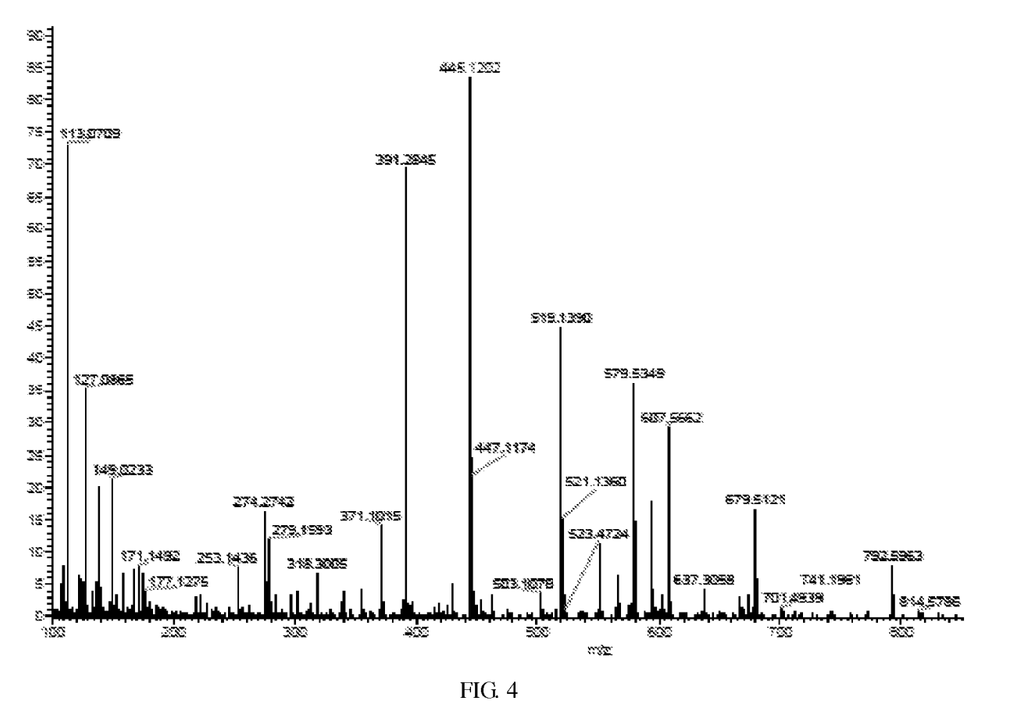
FIG. 4 is a molecular mass of small molecular aromatics from the catalytic one-pot hydrolytic depolymerization of lignocellulose, but the reaction temperature is raised to 250° C. directly.

The isolation method for small molecular aromatics is described in EXAMPLE 3. For the reaction where the temperature is raised to 180° C. and maintained at this temperature for ten minutes, then increased to 250° C. and stirred for 50 min. GC analysis shows there is no phenols formed, and molecular weight analysis shows that it is the same as in FIG. 3, most of them have molecular weight below 400. For the reaction where the temperature is heated to 250° C. directly and stirred at this temperature for 50 min. GC analysis shows that the product contains phenol (0.2-1.5 g/L), methoxyphenol (0.1-1.1 g/L), 2,6-dimethoxyphenol (0.2-2.0 g/L). The analysis of molecular weight shows that most of the aromatics have a molecular weight higher than 400 (FIG. 4).

The difference between the molecular weights of small molecular aromatics suggests that it is critical for the temperature to be heated to 180° C. and maintained for ten minutes for the lignin hydrolysis. The distribution of small organic acids and the formation of phenols suggest that it is also critical for the temperature to be heated to 180° C. and maintained for ten minutes for the selectivity of lactic acid.

Example 5

The product A is titrated with potassium hydroxide solution in methanol until pH=11. All liquids are removed under reduced pressure with heating temperature maintained below 100 degrees Celsius. Solid product B (it is potassium salts of small molecular aromatics) is obtained.

To a 1 liter stainless steel autoclave equipped with mechanical stirrer, add 900 ml of distilled water, 18 g of chopped dry grape tree branches (2-10 mm size, contain 38% cellulose, 20% hemicellulose, 29% lignin, and 13% others), and 10 g of product B. The autoclave is sealed, purged with nitrogen three times, then filled with nitrogen at a pressure of 0.2-1 MPa, heated to 180° C. and maintain at this temperature for ten minutes. The temperature is then increased to 250° C., and stirred at this temperature for 50 min. After cooling to a temperature below 60° C., a brown colored solution is obtained (the color darkens after the mixture is exposed to air). Gas is sampled for GC analysis. There is no alkanes or alkenes are detected in gas phase, and only trace of carbon monoxide. So there is no gasification. Filtration shows no signs of solid material in the product solution, concluding that the percentage of hydrolytic depolymerization is about 100%.

GCMS analysis shows there are almost no phenols, such as phenol, o-methoxyphenol, 2,6-dimethoxyphenol, etc. HPLC analysis of the solution shows that only several small organic acids are formed, such as formic acid, glycolic acid, acetic acid, lactic acid, succinic acid, etc. It contains 5.5 grams of lactic acid, 1.8 grams of glycolic acid, 1.66 grams of formic acid, 0.3 grams of acetic acid, 0.3 grams of succinic acid, and the rest are 2-hydroxyl isobutyric acid, fumaric acid, etc.

The reaction solution is concentrated to about 100 ml under reduced pressure; the liquid obtained is mixed with equal volume of benzyl alcohol and acidified with formic acid to pH=4.2. The organic phase is separated and washed once with a half volume of water. HPLC analysis shows there is no organic acid in organic solution. The benzyl alcohol is carefully removed under reduced pressure to obtain 20 g of sticky products (Product A). GC analysis shows it contains 75% benzyl alcohol. The weight of the small aromatics obtained is 15.3 g (subtracts product B 10 grams=5.3 g)—its yield is 100% based on lignin weight. Molecular mass analysis shows they are mixtures (FIG. 3), most of which with a molecular weight between 162 to 340. GC analysis shows there are no phenol, methoxyphenol, and 2,6-dimethoxyphenol. Elemental analysis shows the oxygen content of this product is 18%, far below the oxygen content of lignin (~36%). This result suggests that our invented method is a catalytic oxygen-transfer reaction; oxygen atoms are transferred from lignin (products from lignin have reduced oxygen content) to cellulose or hemicellulose.

After extraction with benzyl alcohol, the aqueous phase is combined with water solution from washing benzyl alcohol extract, acidified with formic acid to pH=2.0 first, then water is carefully removed with toluene to obtain 16.2 g of organic acid products. There is almost no water left, and toluene content is less than 1%. Subtract the weight of catalyst, the yield of organic acid is about 100%.

Experiments with other salts, such as sodium and calcium, are also carried out using the exact same procedure, same results are obtained. These results show that the metallic salts of small molecular aromatics obtained from the hydrolytic depolymerization of lignocelluloses are effective catalysts.

Example 6

The experiments are carried out using the procedure described in example 4. Chopped fresh grape tree branches are used, with different programmed temperatures and reaction time; the results are tabulated below (The reaction time at 250° C. are the same, all the data is at least the average of three experimental results):

| | Temperature (° C.) | Time (minutes) | % of small molecular aromatics with molecular weight less than 400 |
|---|---|---|---|
| 1 | 175 | 10 | 85 |
| 2 | 177 | 10 | 87 |
| 3 | 179 | 10 | 90 |
| 4 | 181 | 10 | 90 |
| 5 | 183 | 10 | 88 |
| 6 | 185 | 10 | 87 |
| 7 | 180 | 10 | 91 |
| 8 | 180 | 6 | 83 |
| 9 | 180 | 9 | 91 |
| 10 | 180 | 12 | 92 |
| 11 | 180 | 15 | 89 |

These results confirm that lignin hydrolysis requires a programmed temperature at 180±5° C. for 10 minutes. For the reactions with a temperature maintained below 170° C. or above 190° C., the products contain a lower amount of small molecular aromatics with molecular weight less than 400.

Example 7

The experiments are carried out using the procedure described in example 1. Chopped fresh grape tree branches are used. The catalysts used are the potassium salts of 9,10-dihydroxyanthracene, 2,6-dihydroxyanthracene, 2-ethyl-9,10-dihydroxyanthracene, 1-nitrodihydroxyanthracene, dihydroxyanthracene-1-sulfonic acid, dantron, emodin, aloe emodin, rufigallol, mitoxantrone, pixantrone, anthracyclines, dinitro-dihydroxyanthracene, C. I. Acid Blue 43, C. I. Vat Violet 1, C. I. Disperse Red 60. The results of analysis show that conversions of all the catalytic one-pot hydrolytic depolymerization are about 100% and the product distribution is the same as to that catalyzed by disulfonate sodium salt of 9,10-dihydroxyanthracene.

Example 8

Different lignocelluloses are used. The experiments are carried out using the procedure described in example 1. The analytic results are tabulated below:

| Biomass | Polymer content (%) | | | Lignin/(Cellulose + Hemicellulose) | Hydrolysis (%) | Organic acid (%) | Small aromatics (%) |
|---|---|---|---|---|---|---|---|
| | Lignin | Cellulose | Hemi-cellulose | | | | |
| Pine | 30 | 49 | 10 | 0.508 | >99 | 60.78 | 25.9 |
| Bamboo | 30 | 45 | 21 | 0.4545 | ~97 | 68.50 | 25.2 |
| Reed | 23 | 50 | 21 | 0.324 | ~92 | 73.1 | 29.5 |
| Cotton stalk | 23 | 41 | 20 | 0.377 | ~93 | 62.8 | 19.8 |
| Rape straw | 22 | 39 | 27 | 0.333 | ~92 | 68.2 | 19.1 |

-continued

| Biomass | Polymer content (%) | | | Lignin/ (Cellulose + Hemicellulose) | Hydrolysis (%) | Organic acid (%) | Small aromatics (%) |
| --- | --- | --- | --- | --- | --- | --- | --- |
| | Lignin | Cellulose | Hemi-cellulose | | | | |
| Sorghum stalk | 19 | 37 | 25 | 0.306 | ~91 | 63.8 | 15.9 |
| Grass | 14 | 56 | 20 | 0.184 | ~85 | 72.0 | 8.5 |

The results show that the ratio of [Lignin/(Cellulose+Hemicellulose)] is important in the percentage of hydrolytic depolymerization.

The invention claimed is:

1. A catalytic method for quantitative one-pot hydrolytic depolymerization of lignocelluloses into smaller organic chemicals, comprising:
    combining lignocelluloses and metallic salts of 9,10-dihydroxyanthracene and its derivatives as a catalyst in water to form a reaction mixture, thereby simultaneously reducing lignin to smaller aromatic molecules and oxidizing cellulose and hemicellulose are into compounds comprising smaller organic acids;
    wherein a ratio of a mass weight of lignin to the combined mass weights of cellulose and hemicellulose is 0.5 or higher in said reaction mixture;
    wherein the temperature of the reaction mixture is maintained in from ambient to 180±5° C. for about ten minutes, then raised to 190° C. to 280° C.;
    wherein no further reductants are added to said reaction mixture to preform said reducing of lignin; and
    wherein no further oxidants are added for oxidizing cellulose or hemicellulose.

2. The catalytic method according to claim 1, wherein the majority of small aromatic molecules have a molecular weight less than 400 Da.

3. The catalytic method according to claim 1, wherein said derivatives of metallic salts of 9,10-dihydroxyanthracene are metallic salts of 1,2-, 1,4-, 2,6-dihydroxyanthracene, 2-ethyl-9,10-dihydroxyanthracene, 1-nitro dihydroxyanthracene, 9,10-dihydroxyanthracene-1-sulfonic acid, dantron, emodin, aloe emodin, rufigallol, mitoxantrone, pixantrone, anthracyclines, dinitro dihydroxyanthracene, C. I. Acid Blue 43, C. I. Vat Violet 1, or C. I. Disperse Red 60.

4. The catalytic method according to claim 1, wherein the catalyst further includes metallic salts of small molecular aromatics that are obtained from one-pot hydrolytic depolymerization of lignocelluloses.

5. The catalytic method according to claim 1, wherein the reaction time of hydrolytic depolymerization is 60±10 minutes.

6. The catalytic method according to claim 1, wherein said lignocelluloses are products of wood plants.

7. The catalytic method according to claim 1, wherein a reaction pressure is a above the vapor pressure of a solvent in said reaction mixture at a reaction temperature.

* * * * *